United States Patent [19]
Mueller et al.

[11] Patent Number: 5,599,696
[45] Date of Patent: Feb. 4, 1997

[54] METHOD OF PREPARING NUCLEIC ACIDS HAVING AN UNDEFINED NUCLEOTIDE SEQUENCE AMPLIFICATION

[75] Inventors: Paul R. Mueller; Paul A. Garrity, both of Pasadena; Barbara J. Wold, San Marino, all of Calif.

[73] Assignee: California Institute of Technology, Oakland, Calif.

[21] Appl. No.: 323,571

[22] Filed: Oct. 17, 1994

Related U.S. Application Data

[63] Continuation of Ser. No. 118,571, Sep. 8, 1993, abandoned, which is a continuation of Ser. No. 803,679, Dec. 3, 1991, abandoned, which is a continuation of Ser. No. 422,652, Oct. 17, 1989, abandoned.

[51] Int. Cl.$^6$ .............................. C12P 19/34; C12Q 1/68
[52] U.S. Cl. ............................................................ 435/91.2
[58] Field of Search ........................................ 435/6, 91.2

[56] References Cited

U.S. PATENT DOCUMENTS

| | | | |
|---|---|---|---|
| 4,321,365 | 3/1982 | Wu et al. | 435/172.3 |
| 4,683,195 | 7/1987 | Mullis et al. | 435/6 |
| 4,683,202 | 7/1987 | Mullis | 435/91 |
| 4,754,065 | 6/1988 | Levenson et al. | 562/564 |
| 4,800,159 | 1/1989 | Mullis et al. | 435/172.3 |

OTHER PUBLICATIONS

Frohman et al., Rapid Production of Full–length cDNAs from Rare Transcripts; Amplification Using a Single Gene-specific Oligonucleotide Primer, Proc. Natl. Acad. Sci. USA 85:8998–9002 (1988).

Loh et al., Polymerase Chain Reaction with Single–Sided Specificity: Analysis of T Cell Receptor & Chain, Science 243:217–220 (1989).

White et al., The Polymerase Chain Reaction, TIG 5:186–189 (1989).

Sarger et al, Proc. Natl. Acad. Sci USA, v. 74, n. 12, Dec. 1977, pp. 5463–5467.

Maniatis et al, Molecular Cloning—A Laboratory Manual, Cold Spring Harbor Laboratory, 1982, pp. 133, 146, 219, 220.

New England BioLabs Price List, Aug. 1989.

*Primary Examiner*—W. Gary Jones
*Assistant Examiner*—Ethan Whisenant
*Attorney, Agent, or Firm*—Poms, Smith, Lande & Rose

[57] ABSTRACT

A method for amplifying specific nucleic acid fragments having an undefined nucleotide sequence wherein said nucleic acid fragments are present in a mixture of nucleic acids. Blunt ended linkers with known nucleotide sequences are used in the method to isolate and distinguish the specific undefined nucleic acid fragments from the rest of the nucleic acid. Primers which hybridize with the known linker are then used as part of a polymerase chain reaction procedure to amplify the specific nucleic acid fragment which includes the undefined nucleotide sequence.

7 Claims, 6 Drawing Sheets

B
5'-OH-GCGGTGACCCGGGAGATCTGAATTC-OH-3'
3'-OH-CTAGACTTAAG-OH-5'

METHOD OF PREPARING NUCLEIC ACIDS HAVING AN UNDEFINED NUCLEOTIDE SEQUENCE AMPLIFICATION

This invention was supported by NIH grant Nos. RR07003 and GM35526, the United States Government may have certain rights in the invention.

This is a continuation of application Ser. No. 08/118,571 filed on Sep. 8, 1993 now abandoned, which is a continuation of Ser. No. 07/803,679 filed on Dec. 3, 1991, now abandoned, which is a continuation of Ser. No. 07/422,652 filed on Oct. 17, 1989, now abandoned.

BACKGROUND OF THE INVENTION

The polymerase chain reaction (PCR) is an in vitro method for producing large amounts of a specific DNA fragment of defined length and sequence from small amounts of a complex template. Recombinant DNA techniques have revolutionized molecular biology and genetics by permitting the isolation and characterization of specific DNA fragments. Many cloning methods can be complemented and sometimes even circumvented by using PCR, and novel applications of the technique now permit studies that were not possible before. Such methods include DNA fragment isolation, fragment endlabeling, mutagenesis, DNase I footprinting, cDNA cloning, genomic cloning, promoter manipulations, DNA sequencing, and RNA and DNA quantitation. The sensitivity, speed and versatility of PCR are having a profound impact on molecular biological approaches to problems in human genetics, forensic science, and evolutionary and developmental biology.

PCR is based on the enzymatic amplification of a DNA fragment that is flanked by two oligonucleotide primers that hybridize to opposite strands of the target sequence. The primers are oriented with their 3' ends pointing towards each other. Repeated cycles of heat denaturation of the template, annealing of the primers to their complementary sequences and extension of the annealed primers with a DNA polymerase result in the amplification of the segment defined by the 5' ends of the PCR primers. Since the extension product of each primer can serve as a template for the other primer, each cycle essentially doubles the amount of the DNA fragment produced in the previous cycle. This results in the exponential accumulation of the specific target fragment, up to several millionfold in a few hours. The method can be used with a complex template such as genomic DNA and can amplify a single-copy gene contained therein. It is also capable of amplifying a single molecule of target in a complex mixture of RNAs or DNAs and can, under some conditions, produce fragments up to ten kbp long. The PCR technology is the subject matter of U.S. Pat. Nos. 4,683,195, 4,800,159, 4,754,065, and 4,683,202 all of which are incorporated by reference herein.

By using the thermostable Taq DNA polymerase isolated from the thermophilic bacterium Thermus aquaticus instead of the E. coli Klenow fragment of DNA polymerase I, it has been possible to avoid inactivation of the polymerase which necessitated the addition of enzyme after each heat denaturation step. This development has led to the automation of PCR by a variety of simple temperature-cycling devices, and consequently the use of PCR has expanded rapidly. In addition, the specificity of the amplification reaction is increased by allowing the use of higher temperatures for primer annealing and extension. The increased specificity improves the overall yield of amplified products by minimizing the competition by nontarget fragments for enzyme and primers.

While the possible uses of PCR are numerous, the applications are limited to those situations where enough is known about the DNA sequence to design two PCR primers which hybridize to opposite strands of the target sequence. Thus, in techniques such as sequencing, footprinting, or cloning promotor elements, where one end of the template is unknown PCR cannot be utilized.

Thus, there exists a need for an effective method to add a uniform, defined sequence which would allow for the use of PCR when only one end sequence is initially known. Such a method could be of critical importance to increasing the efficiency of sequencing the human genome. The present invention satisfies this need and provides related advantages as well.

SUMMARY OF THE INVENTION

The present invention is directed to a method of amplifying a nucleic acid having an undefined nucleotide sequence comprising:

(a) hybridizing a first nucleotide primer for the undefined sequence;

(b) extending the first primer to the terminus of the undefined sequence to create a complementary double stranded nucleic acid having a blunt end;

(c) ligating at least one strand of a double stranded nucleic acid linker having a defined length and at least a partially defined nucleotide sequence to the blunt end in proper orientation;

(d) denaturing the ligated double stranded nucleic acid to create single stranded nucleic acids;

(e) hybridizing to a single stranded nucleic acid of (d) a second nucleotide primer for the undefined sequence;

(f) extending the second primer to the terminus of the sequence to create a double stranded nucleic acid;

(g) denaturing the double stranded nucleic acid of (f) to create single stranded nucleic acids;

(h) hybridizing a nucleotide primer for the undefined sequence of each single stranded nucleic acid of (g); and (i) extending the hybridized primers of (h).

BRIEF DESCRIPTION OF THE FIGURES

FIG. 4A shows the visualization of gel analysis where a single-stranded Eco RI-Dde I fragment was amplified from 1 Mg DNA per base-specific reaction using primer set D. The amplified DNA was split for gel electrophoresis with the four rightmost lanes receiving 2.5 times more DNA than the four leftmost lanes in order to visualize the weakest bands. The strong signal in all lanes at position—436 of FIG. 4A corresponds to the Eco RI site at which the DNA had been cut. The sequence corresponds to the published sequence except at position—430, where there is an extra A.

FIG. 4B shows the results of gel analysis where rehybridization of the nylon membrane with a single-stranded XmaII-Pvu II fragment allowed visualization of the sequence defined by set F. The amplified DNA was also split for gel electrophoresis with the four rightmost lanes receiving 2.5 time more DNA than the four leftmost lanes.

DETAILED DESCRIPTION OF THE INVENTION

The term "undefined sequence" as used herein refers to a nucleic acid in which all or a portion of the nucleotide sequence is not known. While the present methods allow for the amplification of even completely known sequences, the methods are especially useful where only one end of a nucleotide sequence is known or partially known. The methods provide a means to create a second defined end such that undefined nucleic acids between the original known sequence and the second defined end can be amplified. The method allows amplification even in cases where a nucleic acid is completely undefined. For example, a probe can be randomly created to hybridize random sequences which can then be amplified.

The term "primer" as used herein refers to an oligonucleotide, whether occurring naturally as in a purified restriction digest or produced synthetically, which is capable of acting as a point of initiation of synthesis when placed under conditions in which synthesis of a complementary nucleic acid is induced, i.e., in the presence of nucleotides and an inducing agent such as DNA polymerase and at suitable temperature and pH. The primer is preferably single stranded for maximum efficiency in amplification, but can alternatively be double stranded. If double stranded, the primer is first treated to separate its strands before being used. Preferably, the primer is an oligodeoxyribonucleotide. The primer must be sufficiently long to prime the nucleic acid synthesis in the presence of the inducing agent. The exact lengths of the primers will depend on many factors, including temperature, source of primer and use of the method.

The primers are hybridized to the different strands of each specific sequence to be replicated or amplified. This means that the primers must be sufficiently complementary to hybridize with their respective strands. However, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer.

The term "linker" as used herein refers to a double stranded nucleic acid whether occurring naturally or produced synthetically which is capable of hybridizing to the blunt end of another blunt ended nucleic acid. At least one of the linker's nucleic acid strands is of a known nucleotide sequence so that a portion of this sequence can serve as a primer. The linker nucleotide sequence can be partially or completely defined so long as the partial sequence is sufficient to hybridize a primer to at least a portion of the sequence to initiate synthesis. The primer can be identical to the linker sequence and thereby obviate the need to isolate or synthesize a further primer sequence. Either or both linker sequences can serve as the linker primer.

The linker must ligate to the blunt ended nucleic acid in "proper orientation". The term "proper orientation" refers to the linker ligating in a defined orientation so that it is capable of replication and can serve as the primer sequence or sequence of primer hybridization for initiation of amplification. This proper orientation can be accomplished by designing the linker to ligate only in one orientation. Single orientation is accomplished, for example, by staggering the linker at one end, while maintaining the blunt end. Since the linker only has one blunt end, it will ligate to the blunt-ended sequence products only in one orientation. In addition, the linker preferably does not self-ligate. Such self-ligation can be prevented, for example by removing the phosphate and/or hydroxyl group from the blunt end of the linker. The linker can be ligated by any effective means. In one effective means, the ligation is accomplished with an enzyme. The enzyme can be a DNA ligase. The present invention is directed to a method of amplifying a nucleic acid having an undefined nucleotide sequence comprising:

(a) hybridizing a first nucleotide primer for the undefined sequence;

(b) extending the first primer to the terminus of the undefined sequence to create a complementary double stranded nucleic acid having a blunt end;

(c) ligating at least one strand of a double stranded nucleic acid linker having a defined length and at least a partially defined nucleotide sequence to the blunt end in proper orientation;

(d) denaturing the ligated double stranded nucleic acid to create single stranded nucleic acids;

(e) hybridizing to a single stranded nucleic acid of (d) a second nucleotide primer for the undefined sequence;

(f) extending the second primer to the terminus of the sequence to create a double stranded nucleic acid;

(g) denaturing the double stranded nucleic acid of (f) to create single stranded nucleic acids;

(h) hybridizing a nucleotide primer for the undefined sequence of each single stranded nucleic acid of (g); and (i) extending the hybridized primers of (h).

Steps (a) through (f) thus provide a method of making a double stranded nucleic acid suitable for polymerase chain reaction amplification from a nucleic acid having an undefined sequence. Additionally, if only steps (a) through (c) are followed, a method of ligating a double stranded nucleic acid having a blunt end to a nucleic acid having an undefined nucleotide sequence is provided.

Additionally, the invention also provides a method of cloning into a vector a nucleic acid having an undefined nucleotide sequence comprising following steps (a) through (i) and further adding to the product of step (i) a restriction enzyme for restriction sites to obtain a cleaved product, and ligating the cleaved product into a cloning vector.

A method of cloning into a vector a nucleic acid having an undefined nucleotide sequence can also be carried out by performing steps (a) through (c) and then ligating the product of (c) into a cloning vector. The vectors may then be used to transform an appropriate host organism to produce the gene product of the sequence by standard methods of recombinant DNA technology.

A method of sequencing a nucleic acid having an undefined nucleotide sequence. The method comprises:

(a) hybridizing a first nucleotide primer for the undefined sequence;

(b) extending the first primer to the terminus of the undefined sequence to create a complementary double stranded nucleic acid having a blunt end;

(c) ligating at least one strand of a double stranded nucleic acid linker having a defined length and at least a partially defined nucleotide sequence to the blunt end in proper orientation;

(d) denaturing the ligated double stranded nucleic acid to create single stranded nucleic acids;

(e) hybridizing, to a single stranded nucleic acid of (d) a second nucleotide primer for the undefined sequence;

(f) extending the second primer to the terminus of the linker sequence to create a double stranded nucleic acid;

(g) denaturing the double stranded nucleic acid of (f) to create single stranded nucleic acids; and (h) sequencing the product of (g).

After (g) a nucleotide primer for the undefined sequence can be hybridized to each single stranded nucleic acid and extended prior to sequencing. Sequencing can be performed by methods well known in the art, for example, Maxam and Gilbert, Methods Enzymol. 65:499 (1980) incorporated by reference herein. Alternatively, the nucleic acid can be cleaved, for example, by the methods set forth in Maxam and Gilbert, supra, prior to steps (a) through (h). This procedure could be done with or without rounds of exponential amplification. The second primer can be labeled to allow visualization. The label can be, for example, radioactive, fluorescent, or enzymatic. Additionally, after step (g), a third primer could be used to indirectly label the nucleic acid. The end-labeled extension products can then be visualized on a standard sequencing gel, for example as described in Mueller et al., Genes Dev. 2:412 (1988). Alternatively, the visualization of the sequence can be performed by blotting, for example as described in Church and Gilbert, Proc. Natl. Acad. Sci. U.S.A. 81:1991 (1984), incorporated by reference herein.

Any source of nucleic acid, in purified or nonpurified form, can be utilized as the starting nucleic acid or acids, provided it contains or is suspected of containing the specific nucleic acid sequence desired. Thus, the process can employ, for example, DNA or RNA, including messenger RNA, which DNA or RNA can be single stranded or double stranded. In addition, a DNA-RNA hybrid which contains one strand of each can be utilized. A mixture of any of these nucleic acids can also be employed, or the nucleic acid produced from a previous amplification reaction using the same or different primers can be so utilized. The specific nucleic acid sequence to be amplified can be only a fraction of a larger molecule or can be present initially as a discrete molecule, so that the specific sequence constitutes the entire nucleic acid. It is not necessary that the sequence to be amplified be present initially in a pure form; it can be a minor fraction of a complex mixture. The starting nucleic acid can contain more than one desired specific nucleic acid sequence which can be the same or different. Therefore, the present process is useful not only for producing large amounts of one specific nucleic acid sequence, but also for amplifying simultaneously more than one different specific nucleic acid sequence located on the same or different nucleic acid molecules.

The primers can be prepared using any suitable method, such as, for example, the phosphotriester and phosphodiester methods, or automated embodiments thereof. In one such automated embodiment diethylphosphoramidites are used as starting materials and may be synthesized as described by Beaucage et al., Tetrahedron Letters 22:1859–1962 (1981). One method for synthesizing oligonucleotides on a modified solid support is described in U.S. Pat. No. 4,458,066. It is also possible to use a primer which has been isolated from a biological source (such as a restriction endonuclease digest).

If the nucleic acid to be amplified contains two strands, it is necessary to separate the strands of the nucleic acid before it can be used as the template, either as a separate step or simultaneously with the synthesis. This strand separation can be accomplished by any suitable method including physical, chemical or enzymatic means. One physical method of separating the strands of the nucleic acid involves heating the nucleic acid until it is completely (>99%) denatured. Typical heat denaturation may involve temperatures ranging from about 80° to 105° C. for times ranging from about 1 to 10 minutes. Strand separation can also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Cold Spring Harbor Symposia on Quantitative Biology, Vo. XLIII "DNA: Replication and Recombination" (New York: Cold Spring Harbor Laboratory, 1978), B. Kuhun et al., "DNA Helicases", pp. 63–67 and techniques for using RecA are reviewed in C. Radding, Ann. Rev. Genetics 16:405–37 (1982). An example of strand separation by chemical means is, if the nucleic acid is DNA, alkali treatment. Such treatment is by well known procedures.

The inducing agent may be any compound or system which will function to accomplish the synthesis, including enzymes. Suitable enzymes for this purpose include E. coli DNA polymerase I, Klenow fragment of E. coli DNA polymerase I, T4 DNA polymerase, Taq DNA polymerase, Sequenase™, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed 5' to 3' from the 3' end, until synthesis terminates at the end of the nucleic acid. There may be inducing agents, however, which initiate synthesis at the 5' end and proceed in the other direction, using the same process as described above.

The steps of a typical embodiment of the invention could be as follows:

Step 1. The starting material is genomic DNA that has been cleaved in such a way that it retains a 5' phosphate at the cleavage site. This can be done at a specific site by using a restriction enzyme, or at random bases by Maxam and Gilbert chemistry or DNase-I treatment. Step 2. The cleaved DNA is denatured and a specific primer is annealed to a region of interest. Step 3. This primer is extended with a processive polymerase such as Sequenase™ to create a blunt end at the random cleavage site. Step 4. A common linker is ligated to this blunt end. Because the linker is staggered on one end, it will ligate to the blunt-ended genomic Sequenase™ products in only one orientation. In addition, the lack of 5' phosphates on the linker prevents linker:linker ligation products from forming which could interfere with subsequent steps in the procedure. Step 5. The DNA is denatured and a second primer is annealed to the genomic DNA. To minimize background, the extending end of the second primer is preferably 3' to the first primer. Step 6. The second primer is annealed to the genomic DNA and then extended through the ligated linker region. Step 7 & 8. The nucleic acid is now a suitable substrate for a PCR reaction. On one end there is a linker sequence which a linker primer can anneal to, and on the other end there is a genomic sequence to which a gene-specific primer can anneal. Only molecules that have both of these sequences will be exponentially amplified (approximately 15,000-fold); while molecules with only one of the sequences will be linearly amplified (approximately 15-fold). The difference between the exponential amplification and background from linear amplification provides a favorable signal to noise ratio. The exponentially amplified fragment is now suitable for cloning. If sequencing or footprinting is to be carried out, Steps 9 and 10 are then followed. Step 9 & 10. For the last extension, a third overlapping primer is used to indirectly label the DNA, and these end-labeled extension products are visualized on a standard sequencing gel. The third primer should preferably have an extending end that is 3' to the last primer, and should overlap the last primer. In order to simplify the reaction, the second primer can be used to indirectly label the DNA (using a radioactively labeled primer in steps 7 & 8). However, this procedure can result in higher background and greater exposure to radiation by the user.

The first and second primer may or may not overlap, but the extending end of the second primer is preferably 3' to the first primer (assuming synthesis is proceeding in a 3' direction). If the primers overlap, the overlap is preferably less than approximately 12 bases. The third primer can completely overlap the second primer and extend a few extra 3' bases. It has surprisingly been found that if the second and third primers do not overlap the labelling extension does not work. Thus the primers must compete for the same binding site. The exact reason for this is unclear, but it may involve the extension of the second primer (as it binds) excluding the hybridization of the third primer. Because of the high temperatures used during the hybridization phase of the PCR cycle, extension probably begins immediately after the primer binds. Alternatively, extension of an upstream primer may displace a downstream primer. If the third primer has a higher melting temperature ($T_m$) than the second primer it can compete better for the overlapping binding site. In general the $T_m$ of the primers should preferably increase from the first primer to the second and the second to the third. If the primer $T_m$ increases, the Sequenase primer (the first primer) will be unstable under the amplification conditions and the amplification primer (the second primer) will be unstable under the labeling conditions. The $T_m$s can be adjusted by changing the GC content and/or the length of the primers.

The linker primer can be part of the linker itself. One example of a suitable linker is of the following structure and sequence:

5'-GCGGTGACCCGGGAGATCTGAATTC-3' 25mer, 60% GC

CTAGACTTAAG-5' 11mer, 36% GC

The longer oligomer (which is ligated to the genomic DNA) contains restriction sites for Bst EII, Sma I, Bgl II, and Eco RI. This oligomer also functions as the linker primer in the PCR amplification. Restriction sites are only important for cloning purposes, and are not used in sequencing or footprinting. The sole function of the 11 mer is to create a blunt end so that T4 DNA ligase can ligate the 25mer to the 5' end of the genomic DNA. By making the short oligomer small and of low GC content, it cannot serve as a primer in subsequent Taq polymerase reactions. Neither of the oligomers have 5' phosphates. The 3' end of the 25mer is ligated to 5' end of the genomic DNA and the 11mer remains unligated. The exact sequence, GC content, length, or type of restriction sites in this linker is not critical. However, the short oligomer should be able to bind to the long oligomer at ligation conditions, but not Taq conditions; the long oligomer should have a $T_m$ in Taq buffer comparable to primer 2 and the linker should be a ligatable structure.

EXAMPLE I

Footprinting Using Ligation Mediated, Single-Sided PCR

Figure 1:
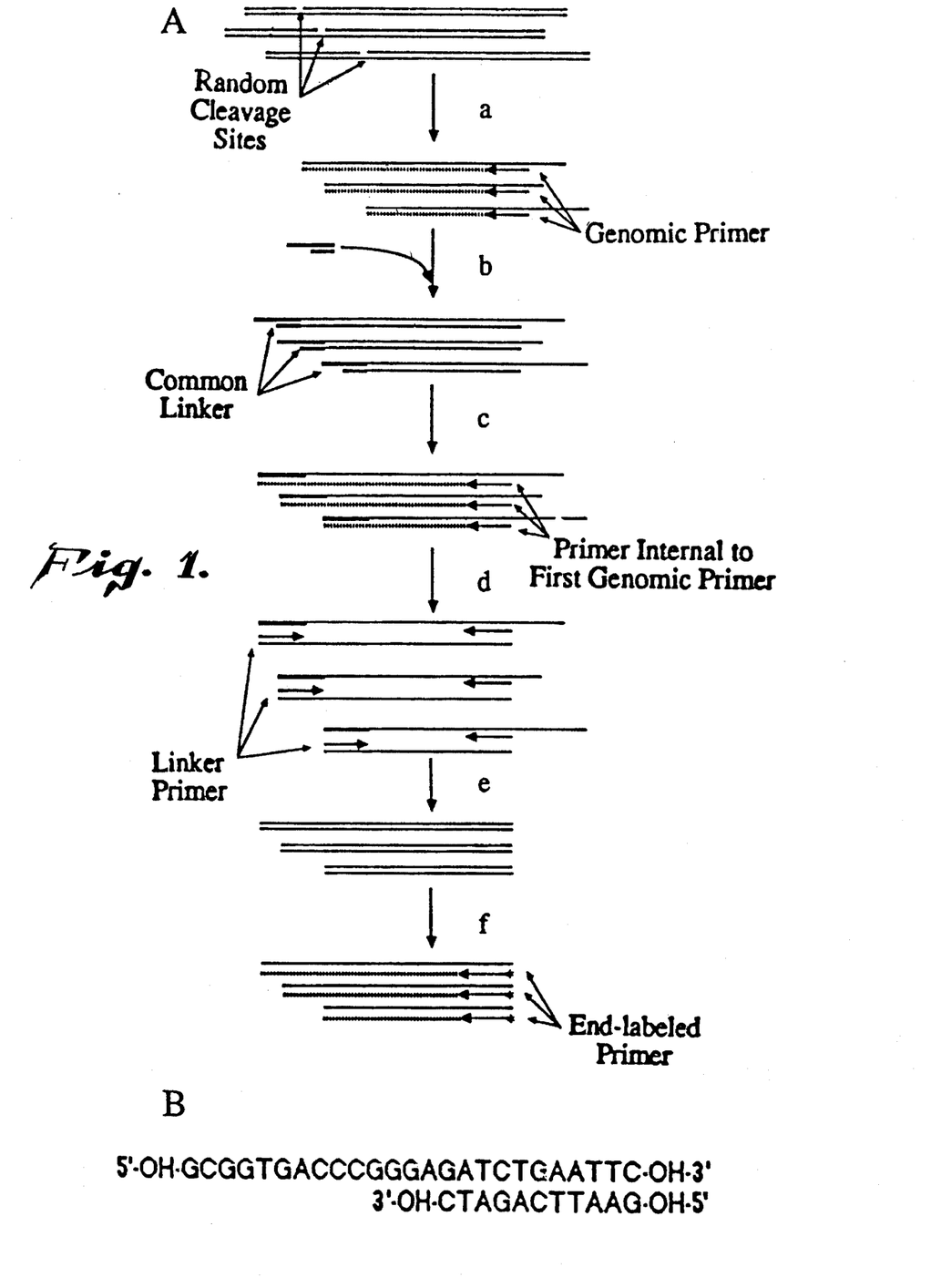
FIG. 1A is a schematic representation of a preferred exemplary method in accordance with the present invention.
FIG. 1B is the nucleotide sequence of a preferred exemplary double-stranded linker.

Schematic of ligation mediated PCR footprinting/sequencing is shown in FIG. 1. (A) Starting material is genomic DNA that has been cleaved by Maxam and Gilbert chemistry, which leaves 5' and 3' phosphates (A. M. Maxam and W. Gilbert, Methods Enzymol. 65: 499 (1980) incorporated by reference herein). The first step (a) defines the fixed end of the sequence ladder by denaturing the cleaved genomic DNA and annealing a gene specific primer. Extension (dotted line) of this primer to the variable cleavage site generates a family of blunt-ended duplex molecules which are substrates for T4 DNA ligase catalyzed addition (b) of a specially designed linker (heavy lines; see below) to each member of the sequence ladder, thereby providing each with a common, defined end. The genomic DNA provides the 5' phosphate used in the ligation. Specificity is provided by the fact that the bulk of the genomic DNA does not serve as a substrate in the ligation reaction because it lacks a blunt double stranded end. The DNA is then denatured (c), and a second gene specific primer is annealed and extended. To increase specificity, the second gene specific primer is positioned so its extending end is 3' to that of the first primer. The original genomic DNA is used again as a template in this reaction, only now it has the longer strand of the linker covalently attached to it, and the extension product reads through this added sequence. Each member of the sequence ladder now has two defined ends (the common linker primer and the second gene specific primer), and is suitable for PCR as described in R. K. Saiki et al., Science 239:487 (1988) and T. J. White et al., Trends Gen. 5:185 (1989) both of which are incorporated by reference herein. After 16 rounds of PCR (d and e), the sequence ladder is amplified approximately $10^4$-fold. It is visualized by primer extension of an end-labeled, third primer (f). Its appearance will be that of the corresponding sequence ladder, except that it will be uniformly longer by the additional length of the linker. The third primer preferably overlaps the second primer, and also is positioned so that its extending end is 3' to that of the second primer. The sequence ladder can also be visualized by filter blotting. (B) Shows the structure of the common linker. The linker shown is but one example of the possible sequences that could be used. It is usually important that: i) the linker contains no 5' phosphates and is staggered to eliminate self-ligation and assure directionality in ligation, respectively; ii) the duplex between the long and short oligomers is stable at ligation conditions, but not at PCR temperatures; and iii) the longer oligomer should have a comparable $T_m$ to that of the second gene-specific primer.

Figure 2:
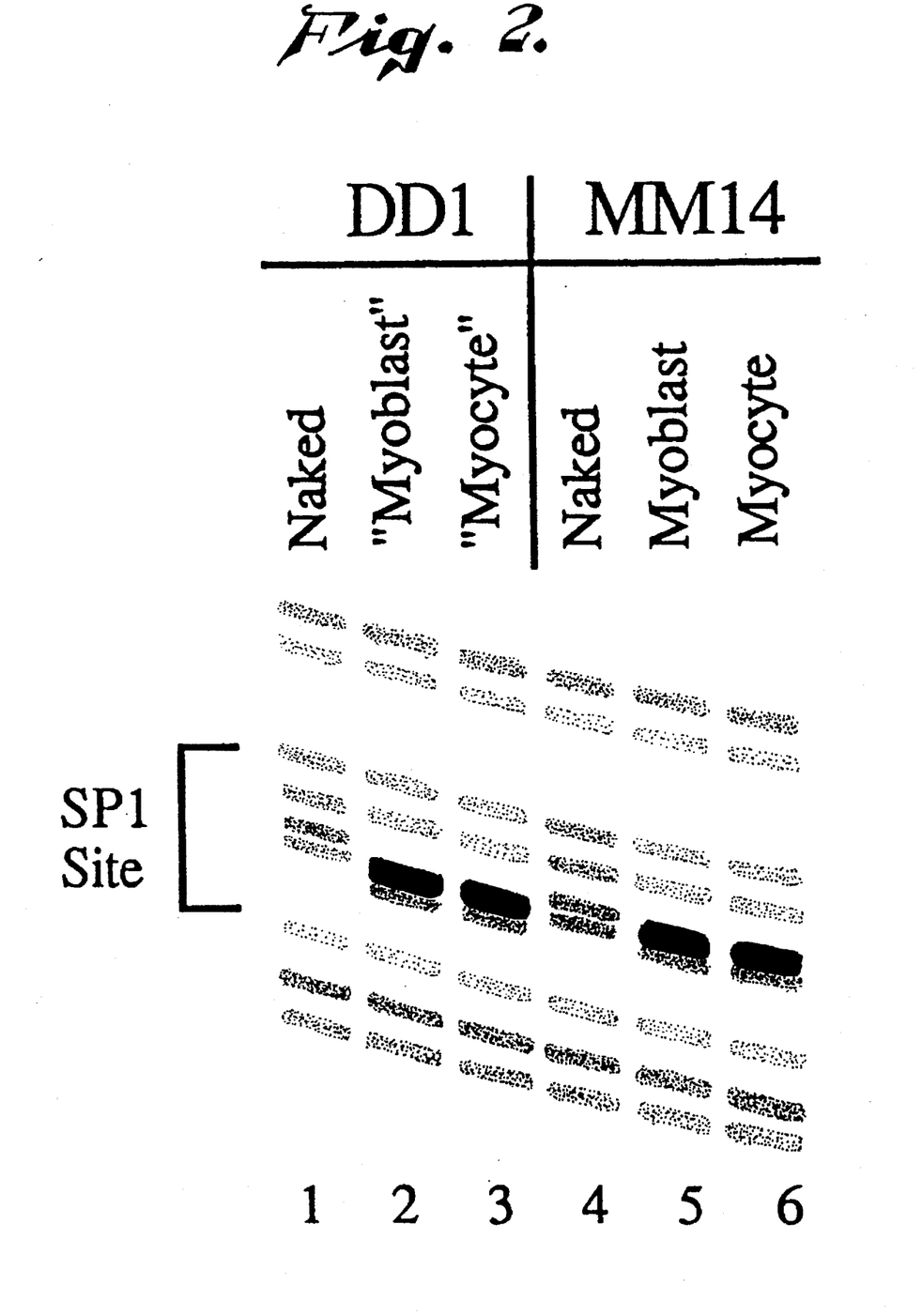
FIG. 2 shows the in vivo footprint of metallochronein-I promoter visualized by ligation mediated, single-sided PCR.

FIG. 2 shows the in vivo footprint of metallothionein-I promoter visualized by ligation mediated, single-sided PCR. A footprint is approximately 185-bp upstream of transcription start on the coding strand of the MT-I promoter (P. R. Mueller et al., Genes Dev. 2:412 (1988) incorporated by reference herein) in both DD1 (lanes 1 to 3) and MM14 (lanes 4 to 6) cells. The Sp1 consensus site is bracketed on left. Naked DNAs are genomic control samples from DD1 or MM14 cells that were treated with DMS in vitro. Myoblast and myocyte DNAs are from the same cells grown under proliferation or differentiation conditions, respectively, and treated with DMS in vivo. In vivo labels for DD1 cells are in quotations because these cells are differentionation defective and therefore do not form true myoblasts or myocytes. All primers and oligomers were gel purified on a 12% standard urea/polyacrylanide gel and soaked out of the polyacrylamide. In the first strand synthesis, 3 µg of DMS/piperidine treated DNA and 0.3 pmol primer 1 (CGGAG-TAAGTGAGGAGAAGGTACTC) were suspended in 15 µl of 40 mM Tris, pH 7.7, 50 mM NaCl. The sample was heated at 95° C. for 2 min, and then incubated at 60° C. for 30 min. Hybridization was stopped by transferring to ice. 7.5 µl of 20 mM MgCl$_2$, 20 mM dithiothreitol (DTT), 0.2 mM of each dNTP was added, then 1.5 µl of a 1:4 dilution of Sequenase™ (United States Biochemical Corp.; Cleveland, Ohio) (diluted in 10 mM Tris pH 7.5 1 mM EDTA) were added, and the sample incubated at 47° C. for 5 min. The reaction was stopped by heating at 60° C. for 5 min, adding 6 µl of 310 mM Tris pH 7.7, and then heating for 10 min at 67° C. In the linker ligation, the sample was transferred to ice, and 20 µl of 17.5 mM MgCl$_2$, 42.3 mM DTT, 125 µg/ml BSA was added, then 25 µl of ligation mix [10 mM MgCl$_2$, 20 mM DDT, 3 mM rATP, BSA (50 µg/ml), with 5 µl PCR linker mix (20 pmol linker per µl in 250 mM Tris pH 7.7, and 3 Weiss units of T4 ligase per 25 µl was added. The oligomers of the linker (see FIG. 1B for sequence) were brought to a final concentration of 20 pmol per µl in 250 mM Tris pH 7.7. (Oligomers were hybridized by heating the solution 95° C. for 5 min and then transferred to 70° C. and slowly cooled (approximately 3 hours) to 4° C. Hybridized linker was stored at −20° C. and thawed on ice.) After incubation overnight at 15° C., the reaction was stopped by heating to 70° C. for 10 min. The sample was then precipitated in the presence of 10 µg carrier yeast tRNA. In the PCR reaction, precipitated samples were washed once with 75% ETOH and brought up in H$_2$O. 20 µl of 5X Taq buffer (200 mM NaCl, 25 mM Tris pH 8.9, 25 mM MgCl$_2$, 0.05% w/v gelatin) was added along with 20 nmoles of each dNTP, 10 pmols of a primer 2 (GGAGAAGGTACTCAGGACGT-TGAAG), 10 pmoles of the longer oligomer of the linker (FIG. 1B), and 5 units of Taq polymerase (Cetus Corp., Emeryville, Calif.). Final volume was adjusted to 100 µl with H$_2$O. Samples were covered with 90 µl mineral oil, heated to 94° C. for 1 min, and then manually cycled (denatured for 1 min at 94° C., hybridized for 2 min at 63° C., extended for 3 min at 76° C.) 16 times. Samples were placed on ice, 1 to 5 pmoles of an end-labeled primer 3 (GAAGTACTCAGGACGTTGAAGTCGTGG) were added, along with 2.5 units Taq polymerase and 20 nmoles of each dNTP (The labeled oligomer was kinased with crude [$^{32}$P] gamma-labeled ATP (DuPont) using T4 polynucleotide kinase (NEB), and unincorporated [$^{32}$P] was removed from it by Nensorb-20 columns (DuPont). Specific activity of the primer was 4×10$^6$ to 9×10$^6$ cpm/pmol). Samples were heated to 94° C. for 2 min, hybridized at 66° C. for 2 min, and extended at 76° C. for 10 min. Polymerase activity was stopped by chilling on ice, adding 295 µl of 260 mM NaOAc, 10 mM Tris pH 7.5, and 4 mM EDTA, and extracting with Phenol/Sevag (1:2). The samples were precipitated, and half of each sample was loaded per lane on a standard sequencing gel as described in A. M. Maxam and W. Gilbert, Methods Enzymol. 65:499 (1987).

In vivo footprints were visualized by comparing samples of DNA that have been exposed to nucleases or alkylating agents in the cell ('in vivo') with samples exposed to these agents after the DNA has been extracted from cells and deproteinized (in vitro or 'naked'). Dimethylsulfate (DMS) is commonly used for this procedure because cell membranes are freely and rapidly permeable to it. Proteins bound to DNA often alter the accessibility of DMS to guanines at or near the binding site. After purification of the DNA, the in vitro and in vivo DMS treated samples are quantitatively cleaved at the methylated guanine residues with piperidine and then compared to reveal the footprint.

The polymerase chain reaction (PCR) uses repeated cycles of template denaturation, primer annealing, and DNA polymerase extension to exponentially amplify the segment of DNA located between two primers. Each cycle doubles the number of templates, and after 25 to 30 cycles a single copy gene can be amplified >10$^6$ fold over the rest of the genome. PCR is not immediately applicable to sequencing or footprinting because it requires two defined ends. A sequence or footprint ladder is composed of a population of related nucleic acid fragments. One end of each fragment is fixed by a primer or restriction cut and is therefore the same for all, whereas the other end is determined by variable chemical cleavage or chain termination and is therefore unique for each fragment. To apply PCR to a sequence ladder, a ligation step that adds a common oligonucleotide sequence to the unique end of each member is utilized. A primer complementary to this new common sequence is then used, together with a primer complementary to the original fixed end, for simultaneous exponential amplification of all members of the sequence ladder. The procedure has a high degree of specificity that derives from the design of the ligation step and the choice of PCR primers (FIG. 1). The method also has high fidelity; a footprint consists of subtle differences in the starting concentrations of particular members of a sequence ladder, and these differences are reproducibly retained through the amplification.

This PCR footprinting technique was tested on the mouse metallothionein-I (MT-I) promoter, which has been well characterized both in vivo and in vitro. Previously, cells containing >100 copies of the MT-I promoter had been used to observe in vivo interactions and a prominent footprint at the upstream Sp1 binding site (Sp1-A) was found. Using PCR footprinting, this region was re-examined in MM14 and DD1 cells that contain only a single copy of the MT-I gene per haploid genome. The expected footprint is apparent in both MM14 and DD1 lines; compare the 'naked' DNA control sample (FIG. 2, lanes 1 and 4) with the in vivo DNA samples from cells grown under either proliferation (lanes 2 and 5) or differentiation (lanes 3 and 6) conditions. This result illustrates the sensitivity of the technique; the data shown are from a 9 hour, screened exposure on Kodak XAR-P film. These footprints correlate with footprints observed as described in Miller et al., Genes Dev. 2:412 (1988), incorporated by reference herein, and establish that the data obtained from ligation mediated PCR footprinting are consistent with more conventional methods.

EXAMPLE II

Genomic Sequencing and Methylation Analysis by Ligation Mediated Single-Sided PRC Step 1 of the genomic sequencing procedure is base-specific chemical cleavage of DNA samples at either G, G+A, T+C, or C, generating 5' phosphorylated molecules. The DNA is from human-hamster hybrid cell lines that contained either an inactive (X8-6T2) or an active (Y162-11C) human X-chromosome as described in R. S. Hansen et al., Mol. Cell. Bio. 8:4692 (1988) incorporated by reference herein. Nuclei were isolated from HeLa (S315) cells by published procedures [J. Wijnholds and J.N.J. Philipsen, G. AB, EMBO J. 7:2757 (1988)], and DNA was purified from the isolated nuclei as described in H. P. Saluz and J. P. Jost, A Laboratory Guide to Genomic Sequencing (Birkhaeuser, Boston, 1987) incorporated by reference herein. DNA's were usually cleaved with EcoRI to reduce viscosity. In the base specific cleavage, DNA, usually 10 µg per reaction, was treated using Maxam-Gilbert reactions as modified by H. P. Saluz and J. P. Jost, A Laboratory Guide to Genomic Sequencing (Birkhaeuser, Boston 1987). After piperidine cleavage, DNA was precipitated with 2.5 volumes of ethanol, washed twice with 80% ethanol, and dissolved in 200 µl water. Traces of piperidine were removed by vacuum-drying the sample overnight. The DNA pellet was dissolved in water (1 µg/µl).

Step 2 is gene-specific primer extension of an oligonucleotide (primer 1) by a DNA polymerase to give molecules which have a blunt end on the side opposite the primer. In the first primer extension, 1 to 2 µg of chemically-cleaved DNA was mixed (final volume 15 µl) with 0.6 pmoles of a gene-specific primer (A1, D1, or F1; see FIG. 3) in 40 mM tris-HCl (pH 7.7) and 50 mM NaCl, heated at 95° C. for 3 min, and then at 45° C. for 30 min. The solution was adjusted to 25 mM tris-HCl (pH 7.7), 30 mM NaCl, 6 mM MgCl$_2$, 6 mM dithiothreitol, 80 µM dNTPs and a final volume of 24 µl. Sequenase™ (4.5 units, USB) was added and the reaction was incubated at 45° C. for 15 min. The reaction was stopped by adding 6 µl of ice-cold 310 mM tris-HCl (pH 7.7), and the enzyme was inactivated at 67° C. for 15 min. The ligation step (11) followed without further treatment.

Step 3 is the ligation of an unphosphorylated linker to the blunt ends. The structure of the linker and the annealing and ligation conditions were as described in Example I.

Step 4 is the exponential amplification of the linker-ligated fragments using the longer oligonucleotide of the linker (linker-primer) and a second gene-specific primer (primer 2) in a PCR reaction. After performing 15 to 18 amplification cycles, the DNA fragments are separated on a sequencing gel, electroblotted onto nylon membranes and hybridized with a single stranded gene-specific probe. This procedure was found to work well for all bases, and sensitivity is improved and background minimized by the transfer and hybridization steps. Moreover, several different sequences can be analyzed in a single experiment by rehybridization of the membrane.

Figure 3:
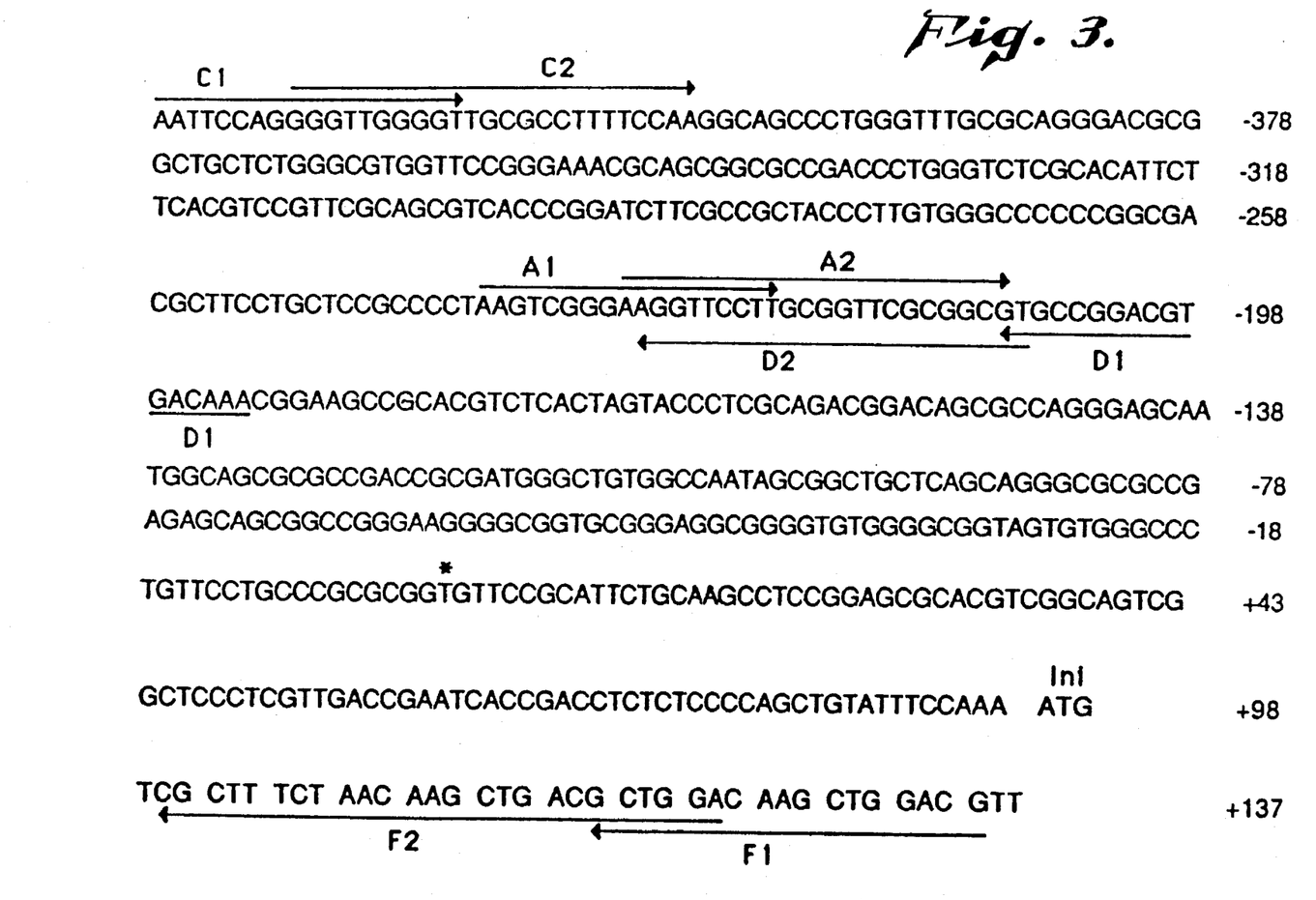
FIG. 3 shows sequence of the CpG island containing the promoter and first exon of the human PGK-1 gene. Arrows indicate the oligonucleotide primer positions and the direction of reading. The asterisk indicates the major transcription start site. Ini marks the translation start point.

In the PCR amplification, Primer extended, ligated molecules were amplified with Taq polymerase (Amplitaq™, Perkin Elmer Cetus) in the presence of the longer oligonucleotide of the linker and a gene-specific primer (A2, D2, or F2; FIG. 3). The fragments were amplified in 100 µl of 10 mM tris-HCl (pH 8.9), 40 mM NaCl, 2 mM MgCl$_2$, gelatin (0.01%), 0.25 mM dNTPs, 10 pmoles of each primer, with 3 units Taq polymerase, according to the Cetus-Perkin Elmer protocol. Thermal cycles, 15 to 18, were done (1 min at 95° C., 2 min at 65° C. and 3 min at 75° C.). Fresh enzyme (1 unit) was added and incubation continued for 10 min at 74° C. EDTA and NaOAc (pH 5.2) were added to 20 mM and 300 mM, respectively, followed by phenol-CHCl$_3$ extraction and ethanol precipitation. DNA pellets were dissolved in electrophoresis sample dye, and just prior to loading, heated at 95° C. for 2 min.

In the gel electrophoresis and electroblotting, DNA fragments were separated on a sequencing gel [95×0.08 or 0.04 cm in 8% polyacrylamide (acrylamide/bisacrylamide, 29:1) and 7M urea], and then transferred to GeneScreen nylon membrane by electroblotting. A simple transfer apparatus was constructed using porous steel plates of a Bio-Rad gel dryer as electrodes and a Bio-Rad 200/2.0 power supply. After the transfer, the membranes were air-dried, baked at 80° C. for 20 min in a vacuum oven, then UV crosslinked (P. B. Becker et al, Cell 51:435 (1987) incorporated by reference herein).

The hybridization was as follows: The cDNA procedure of F. Weih et al., Nucl. Acids Res. 16:1628 (1988) incorporated by reference herein, was used. Small (100 to 200 bp) restriction fragments from the 5' region of PGK-1 were subcloned into Bluescript SK+ (Stratagene, San Diego, Calif.) and then RNA was produced from the inserts on a preparative scale, using either T3 or T7 RNA polymerase. Labeled cDNA was made from the RNA (0.5 µg) by reverse transcriptase using T7 or T3 primers and 100 µCi of [32P] dCTP (6,000 Ci/mmole). After ethanol precipitation, the single-stranded cDNA probe ($1\times10^9$–$5\times10^9$ dpm/µg) was used directly for hybridization. Hybridization probes were made from three subclones, that contained fragments: EcoR I-Dde I (197 bp; positions –436 to –240); Mae III-Apa I (181 bp; –199 to –19), or Xma III-Pvu II (150 bp; –69 to +81). Hybridization and washing buffers were as described in Saluz and Jost, supra. Prehybridization (25 ml hybridization buffer, 10 min) and hybridization (50 µCi per gel in 5 ml hybridization buffer, overnight) were performed in rolling cylinders 68° C. in a hybridization oven (Bachofer, Reutlingen, F.R.G.). Nylon filters were exposed for 2 to 7 hours to Kodak XAR-5 film with intensifying screens at –70° C. For rehybridization experiments, probes were stripped from the membrane by incubation in 0.2M NaOH at 45° C. for 30 min.

Figure 4A:
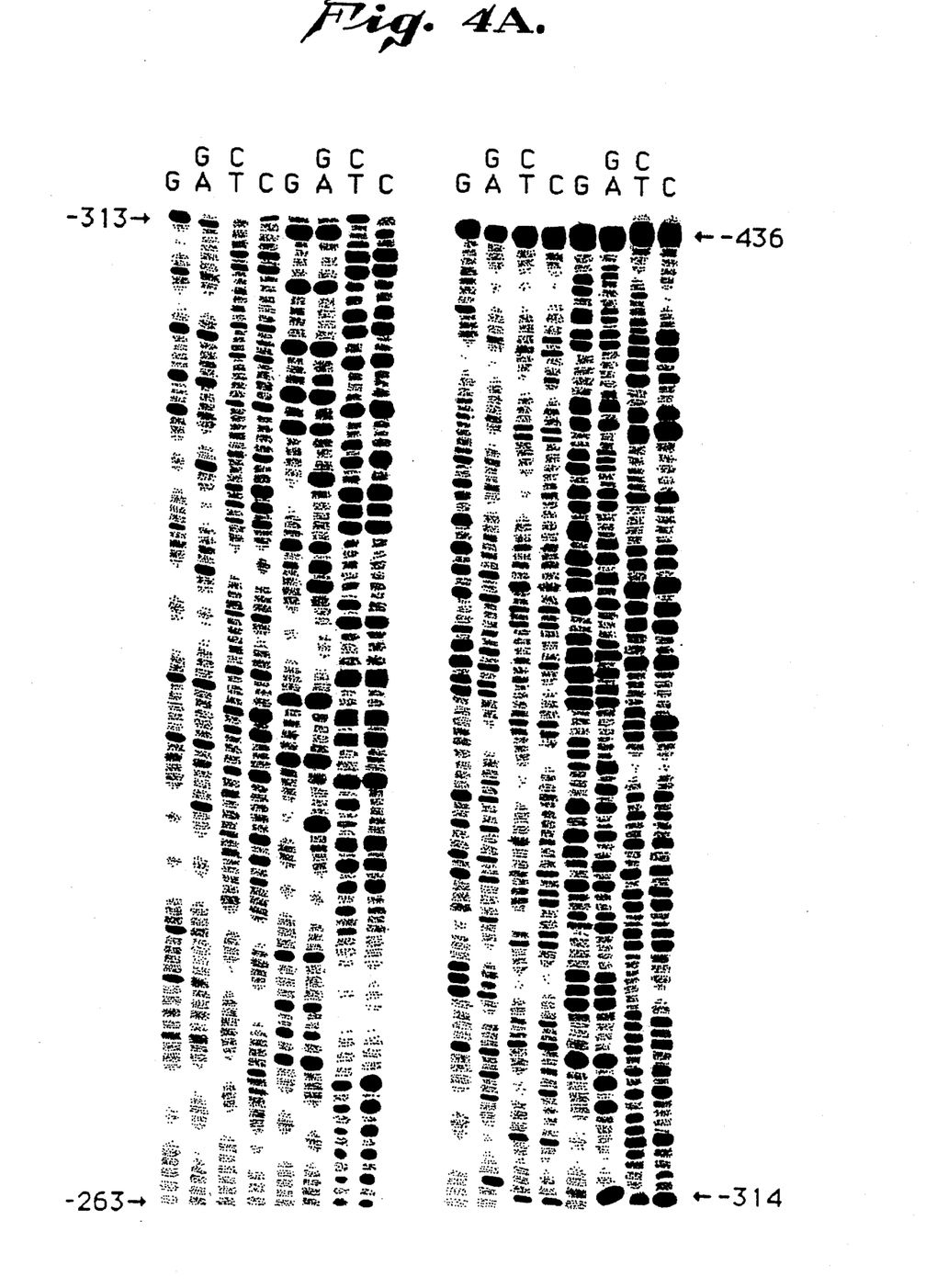
FIG. 4A shows genomic sequence data for the 5' end of PGK-1 in HeLa DNA.
Figure 4B:
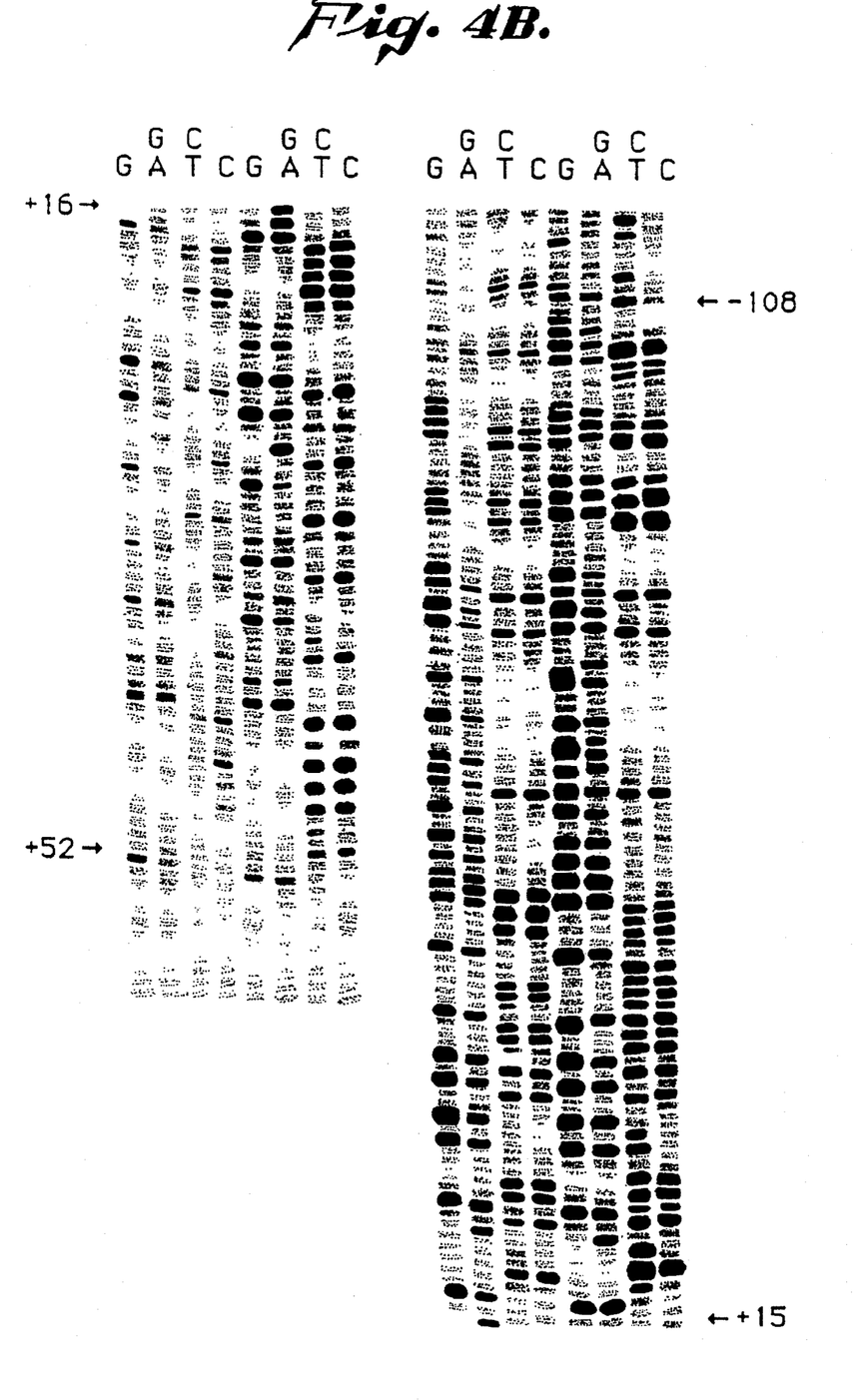
FIG. 4B also shows genomic sequence data for the 5' end of PGK-1 in HeLa DNA.

The 5' region of the human X-linked phosphoglycerate kinase (PGK-1) gene is shown in FIG. 3. PGK-1 is a housekeeping gene that is subject to X inactivation. The 5' region is a CpG-rich island, but unlike most autosomal CpG islands that are characteristically unmethylated, the Hpa II sites in the region shown are methylated on the inactive X chromosome. FIG. 4 shows genomic sequence data for this region obtained from HeLa cell DNA by ligation-mediated PCR. For this experiment two different primer sets (D and F; see FIG. 3) were included simultaneously in the primer extension and amplification reactions. The sequence defined by primer set D was visualized first (panel A) by hybridization with an Eco RI-Dde I hybridization probe. After stripping of the first probe from the membrane and rehybridization with an Xma III-Pvu II probe, the sequence defined by primer set F became visible (panel B). With two loadings as shown, both sequences could be read unambiguously; the correct calls would be made for a total of 336 nucleotides, even if the sequence were not known.

Figure 5:
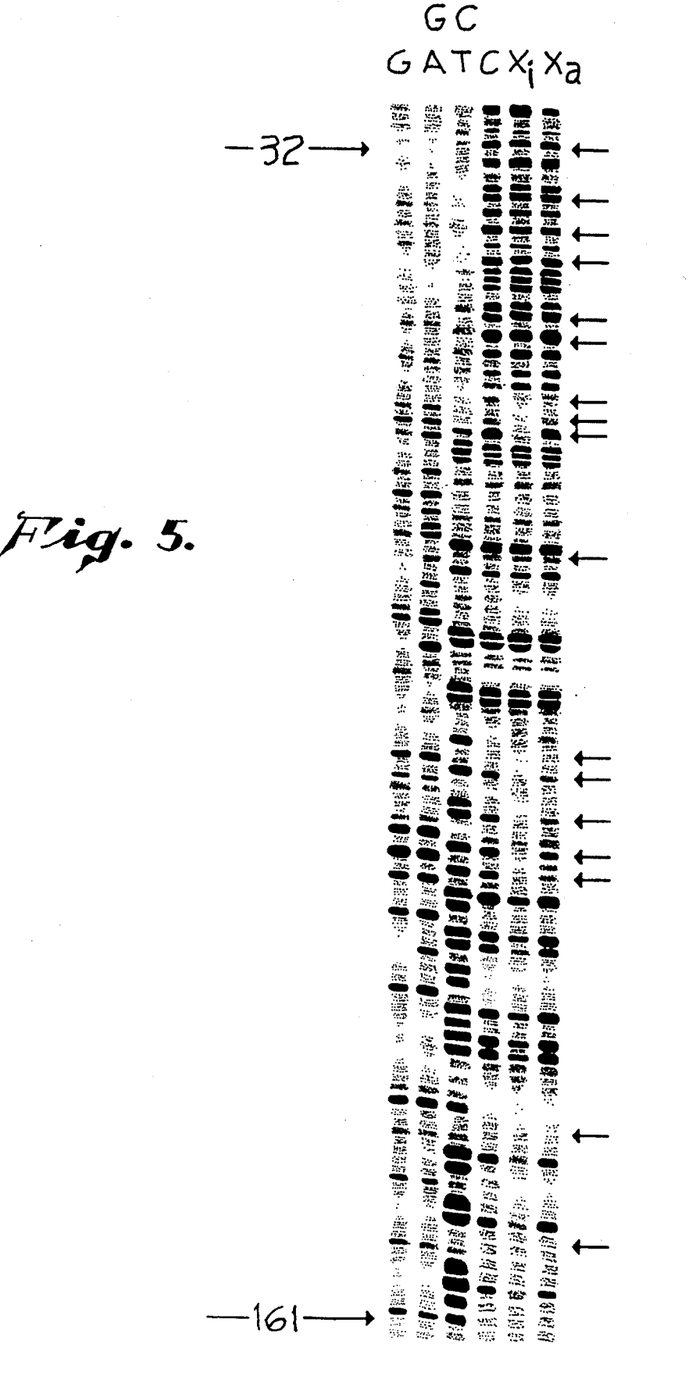
FIG. 5 shows genomic sequence data for HeLa cell DNA and Chinese hamster-human hybrid cell DNA. The lanes labeled G, G+A, T+C, and C show results obtained with 2 µg of HeLa DNA per lane. Oligonucleotides A1 and A2 were used as primers and a single-stranded Mae III-Apa I fragment was the hybridization probe. From the bottom of the gel to the top, the sequence reads the lower stand 3' to 5'. Also shown are C lanes for DNA (2 µg) from hamster-human hybrid cells containing either an active (Xa) or an inactive (Xi) human X-chromosome. Methylated cytosines, which appear as a gap in the sequence ladder, are indicated by arrows.

5-methylcytosine appears as a gap in the cytosine ladder of a Maxam-Gilbert sequencing gel. To test the procedure as an assay for methylated cytosines, human-hamster hybrid cell lines that contained either an inactive or an active human X-chromosome were studied. Primer set A (FIG. 3) allowed reading of the sequence towards the transcription start site, and the data indicate that the human inactive X-chromosome is methylated at all 17 CpG-dinucleotides in the investigated region (FIG. 5, lane Xi), whereas the active X-chromosome is unmethylated at the same 17 sites (FIG. 5, lane Xa). By comparison with cloned DNA, we found that HeLa DNA has no detectable methylation at 52 CpG-dinucleotides analyzed in the PGK-1 associated CpG-rich island, a result consistent with this cell line not having an inactive X-chromosome.

Although the band patterns shown in FIGS. 4 and 5 are reproducible, band intensities vary from fragment to fragment within a single lane; a few bands are weak or even missing on short exposures. For example, 3 bands in a region of about 100 nucleotides are not seen in the sequence shown in FIG. 5. Band intensity may vary because: (i) the chemical reactivity of individual bases may differ; (ii) small effects of sequence on amplification efficiency may play some role, although PCR can be very quantitative and reproducible [±4% SD through 25 cycles]; (iii) certain sequences may not be extended to a blunt end as efficiently in primer extension prior to ligation; (iv) the ligation step may introduce some bias. Overexposed autoradiograms can often be used to obtain sequence information even from weak bands. This is the case for most of the sites studied, for example the CpG site at nucleotide position—119. The intensities of only the weak bands were increased by increasing the time for ligation or the temperature of the first primer extension reaction. Thus, the steps before the PCR may be very efficient for strong bands.

Exponential amplification works so well that band detection probably no longer limits sensitivity. Comparing band intensities with the standard genomic sequencing method applied to the same PGK-1 sequence studied with primer set D, an amplification of 3,000 to 6,000-fold after 15 PCR cycles is estimated (10–20% overall efficiency). One µg of HeLa DNA per reaction gave a strong signal with short exposures (2 hours in FIG. 4B). However, a statistical limit should be considered. The lowest limit of the DNA needed for sequence analysis is a single molecule for each band in the sequence ladder. For optimum efficiency of molecule usage, there should be one chemical cleavage per length of sequence to be analyzed, for example, 1 cut per 200 nt. To avoid band intensity variation of more than 10% standard deviation due only to statistical sampling fluctuation, about 100 founder molecules are needed for each band. If ligation and first primer extension for an unfavorable fragment is only about 10% efficient, then $2\times10^5$ molecules ($200\times100\times10$) should give a band of invariant intensity. This then would be a statistical limit for experiments where visualization of this band is important. Efforts at further increasing the sensitivity of the method should focus on weak bands and on the steps prior to PCR, such as ligation and first primer extension. Increasing ligation time was helpful; however, attempts to increase ligation efficiency by adding polyethylene glycol or hexamine cobalt to the ligation mixtures were unsuccessful. The optimum temperature and $Mg^{2+}$ concentrations for PCR depend on the primer and the gene region to be studied. Optimization of conditions was more critical for certain primers than for others. We obtained good sequence ladders for each of the 4 primer sets in FIG. 3, even though the region is over 70% G+C.

Instead of directly labeling the fragments of the sequence ladder as in Example I, the fragments were transferred to nylon membranes and, to visualize the sequence, hybridized with a single-stranded probe located 3' to the gene-specific primers. Transfer to membranes allows the use of relatively low levels of radioactivity, results in minimal radiation exposure to laboratory workers, and permits analysis of multiple sequences by rehybridization of the membrane (FIG. 4A and B). It is not yet known what the limit is for simultaneous ladder formation and sequential visualization, but a membrane containing a sequence ladder can be rehybridized up to 50 times.

Although the invention has been described with reference to the presently-preferred embodiments, it should be understood that various modifications can be made without departing from the spirit of the invention. Accordingly, the invention is limited only by the following claims.

We claim:

1. A method for selectively amplifying single-stranded nucleic acid fragments having an undefined nucleotide sequence wherein said single-stranded nucleic acid fragments are present in a mixture of nucleic acids, said method comprising the steps of:

providing a mixture of nucleic acids, said mixture comprising a plurality of single-stranded nucleic acid fragments having 3' ends and 5' ends, wherein at least one of said single-stranded nucleic acid fragments has a nucleotide sequence which comprises a defined region and an undefined region and wherein said nucleotide sequence has a terminus located in said undefined region and wherein said terminus is located at the 5' end of said single-stranded nucleic acid fragment;

providing a first primer which comprises an oligonucleotide having a nucleotide sequence which is complementary to a first primer segment located in said defined region of said single-stranded nucleic acid fragment;

hybridizing said first primer to the first primer segment of said single-stranded nucleic acid fragment to provide a single-stranded nucleic acid segment having said terminus on said 5' end and said first primer on said 3' end;

synthesizing a complementary nucleic acid segment which is complementary to said single-stranded nucleic acid segment, said single-stranded nucleic acid segment and said complementary nucleic acid segment forming a double-stranded nucleic acid fragment having a blunt end located at said terminus;

providing a double-stranded linker which comprises first and second complementary linker oligonucleotides wherein at least one of said linker oligonucleotides comprises a known nucleotide sequence, said double-stranded linker having only one end which is capable of being attached to the blunt end of said double-stranded nucleic acid fragment;

attaching said linker to the blunt end of said double stranded nucleic acid fragment to form a double stranded nucleic acid segment having said linker on one end and said first primer on the other end;

separating said double stranded nucleic acid segment into two single-stranded sequences wherein each of said sequences has a first or second linker oligonucleotide at one end and a defined oligonucleotide segment at the other end, said defined oligonucleotide segment comprising said first primer or said defined region;

adding to at least one of said single-stranded sequences a linker primer and a gene-specific primer; and amplifying said at least one of said single-stranded sequences by the polymerase chain reaction to provide amplification of said nucleic acid fragment present in said mixture of nucleic acids.

2. A method according to claim 1 wherein said first linker oligonucleotide is longer than said second linker oligonucleotide to thereby provide a double stranded linker having a blunt end and a staggered end wherein the blunt end of said linker is attached to said double-stranded nucleic acid fragment.

3. A method according to claim 2 wherein neither of said first or second linker oligonucleotides includes a phosphate group on the blunt end of said double-stranded linker.

4. A method according to claim 2 wherein neither of said first or second linker oligonucleotides includes a 3' hydroxyl group on the blunt end of said double-stranded linker.

5. A method according to claims 1 wherein one of said single-stranded nucleotide fragments comprises said first linker oligonucleotide on said 5' end and said defined region on said 3' end, said method including the steps of:

providing a second primer which comprises an oligonucleotide having a nucleotide sequence which is complementary to a second primer segment located in said defined region of said single-stranded nucleotide fragment;

hybridizing said second primer to the second primer segment of said single-stranded nucleotide fragment to provide a second single-stranded nucleic acid segment having said first linker on said 5' end and said second primer on said 3' end;

synthesizing a second complementary nucleic acid segment which is complementary to said second single-stranded nucleic acid segment, said second single-stranded nucleic acid segment and said second complementary nucleic acid segment forming a second double-stranded nucleic acid fragment;

separating said second double-stranded nucleic acid fragment into two defined single-stranded sequences having known oligonucleotide sequences at each end; and adding to at least one of said defined single-stranded sequences a linker primer and a gene-specific primer; and amplifying said at least one of said defined single-stranded sequences by the polymerase chain reaction.

6. A method according to claim 5 wherein at least a portion of said second primer segment overlaps said first primer segment and wherein said second primer segment is located nearer to said terminus than said first primer segment.

7. A method according to claim 5 wherein said second primer segment overlaps said first primer segment and wherein at least a portion of said second primer segment is located nearer to said 5' end of said single-stranded nucleic acid fragment than said first primer segment.

* * * * *